US012576287B2

(12) United States Patent (10) Patent No.: US 12,576,287 B2

Ebina et al. (45) Date of Patent: Mar. 17, 2026

(54) CIRCULAR ACCELERATOR AND PARTICLE BEAM TREATMENT SYSTEM

(71) Applicant: Hitachi High-Tech Corporation, Tokyo (JP)

(72) Inventors: Futaro Ebina, Tokyo (JP); Kenji Miyata, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 291 days.

(21) Appl. No.: 18/286,330

(22) PCT Filed: Jul. 25, 2022

(86) PCT No.: PCT/JP2022/028641
§ 371 (c)(1),
(2) Date: Oct. 10, 2023

(87) PCT Pub. No.: WO2023/013458
PCT Pub. Date: Feb. 9, 2023

(65) Prior Publication Data
US 2024/0198138 A1 Jun. 20, 2024

(30) Foreign Application Priority Data

Aug. 3, 2021 (JP) ................................. 2021-127695

(51) Int. Cl.
*A61N 5/10* (2006.01)
*H05H 13/00* (2006.01)
(52) U.S. Cl.
CPC ........... *A61N 5/1081* (2013.01); *H05H 13/00* (2013.01)
(58) Field of Classification Search
CPC ............................. A61N 5/1081; H05H 13/00
See application file for complete search history.

(56) References Cited

U.S. PATENT DOCUMENTS 10,548,212 B2 * 1/2020 Aoki ...................... H05H 13/04
2019/0239333 A1 8/2019 Aoki
(Continued)

FOREIGN PATENT DOCUMENTS

CN 111279801 A 6/2020
CN 117356173 A 1/2024
(Continued)

OTHER PUBLICATIONS

Extended European Search Report received in corresponding European Application No. 22852882.4 dated May 15, 2025.
(Continued)

*Primary Examiner* — Nicole M Ippolito
(74) *Attorney, Agent, or Firm* — MATTINGLY & MALUR, PC

(57) ABSTRACT

There is provide a circular accelerator and a particle beam therapy system that can improve the beam extraction efficiency. A circular accelerator that accelerates and extracts charged particle beams circulating in a magnetic field includes a first magnetic field region in which closed trajectories of the beams with different energies are eccentric and which has a magnetic field gradient decreasing in the magnetic field toward an outer peripheral side and a second magnetic field region having a magnetic field gradient increasing in the magnetic field toward the outer peripheral side. A border between the first magnetic field region and the second magnetic field region is located on a downstream side in a traveling direction of the beam with respect to a predetermined region in which an interval between the closed trajectories of the beams with the different energies is narrowest.

5 Claims, 7 Drawing Sheets

(56)    References Cited

U.S. PATENT DOCUMENTS

| 2021/0195725 A1* | 6/2021 | Hae | .......................... | A61N 5/10 |
| 2021/0196984 A1* | 7/2021 | Hae | .......................... | H05H 7/04 |
| 2023/0105721 A1 | 4/2023 | Hae et al. | | |
| 2024/0244737 A1 | 7/2024 | Hori et al. | | |

FOREIGN PATENT DOCUMENTS

| EP | 4 358 653 A1 | 4/2024 |
| JP | 2019-133745 A | 8/2019 |
| JP | 2020-038797 A | 3/2020 |
| JP | 6714146 B2 | 6/2020 |
| JP | 2021-007645 A | 1/2021 |

OTHER PUBLICATIONS

Chinese Office Action received in corresponding Chinese Application No. 202280019016.X dated Jan. 29, 2026.

* cited by examiner

CIRCULAR ACCELERATOR AND PARTICLE BEAM TREATMENT SYSTEM

TECHNICAL FIELD

The present invention relates to a circular accelerator and a particle beam therapy system.

BACKGROUND ART

A particle beam therapy is performed in which a charged particle beam (hereinafter, simply referred to as a beam) is accelerated by an accelerator such as a synchrotron or a cyclotron, and the accelerated beam is applied to a lesion such as cancer (PTL 1). PTL 1 describes a circular accelerator that accelerates and extracts a beam circulating in a static magnetic field and a particle beam therapy system using the same.

CITATION LIST

Patent Literature

PTL 1: JP 2019-133745 A

SUMMARY OF INVENTION

Technical Problem

In the circular accelerator described in Patent Literature 1, circular closed trajectories (hereinafter, referred to as central trajectories) formed by beam particles having different kinetic energies (hereinafter, simply referred to as energies) in a static magnetic field are arranged so as to be eccentric toward a beam extraction port from the accelerator, and beams having different energies are extracted from the same beam extraction port to the outside of the accelerator.

Further, the circular accelerator described in PTL 1 accelerates a beam (hereinafter, referred to as a circulating beam) circulating in the accelerator to a desired energy and then applies a radiofrequency voltage in a direction (hereinafter, in the horizontal direction) perpendicular to a beam traveling direction and a magnetic pole gap direction (hereinafter, the vertical direction) to the circulating beam. The beam particle to which the radiofrequency voltage is applied gradually increases in the horizontal amplitude of the oscillation (hereinafter, betatron oscillation) centered on the central orbit and comes into contact with a magnetic field distribution for generating the resonance of the betatron oscillation called the peeler magnetic field and the regenerator magnetic field formed around the central orbit. Beam particles in contact with the peeler magnetic field and the regenerator magnetic field rapidly increase in the amplitude of the betatron oscillation in the horizontal direction, enter the septum magnetic field for extraction, and are extracted to the outside of the accelerator.

Therefore, the circular accelerator described in PTL 1 is an accelerator that accelerates a beam in a static magnetic field but can switch the energy of the beam extracted from the accelerator in a predetermined range (for example, 70 MeV to 230 MeV).

On the other hand, in the circular accelerator described in PTL 1, the oscillation of beam particles diverge in the vertical direction during the extraction of the beam, and the beam particles are lost in the accelerator, so that the beam extraction efficiency from the accelerator may be reduced. The decrease in the beam extraction efficiency leads to a decrease in the beam current emitted from the accelerator and an increase in the treatment time of the particle beam therapy system using the accelerator.

The present invention has been made in view of the above problems, and an object thereof is to provide a circular accelerator and a particle beam therapy system that can improve the beam extraction efficiency.

Solution to Problem

In order to solve the above problem, a circular accelerator according to the present invention is a circular accelerator that accelerates and extracts charged particle beams circulating in a magnetic field. The circular accelerator includes a first magnetic field region in which closed trajectories of the beams with different energies are eccentric and which has a magnetic field gradient in which a magnetic field becomes weak toward an outer peripheral side, and a second magnetic field region in which the magnetic field becomes strong toward the outer peripheral side. A border between the first magnetic field region and the second magnetic field region is located on a downstream side in a traveling direction of the beam with respect to a predetermined region in which an interval between the closed trajectories of the beams with different energies is narrowest.

Advantageous Effects of Invention

According to the present invention, since the gradient of the first magnetic field and the gradient of the second magnetic field simultaneously increase when the amplitude of the horizontal betatron oscillation increases, it is possible to maintain the balance between the convergence force and the divergence force in the vertical direction acting on the beam and to suppress beam loss.

DESCRIPTION OF EMBODIMENTS

Figure 1:
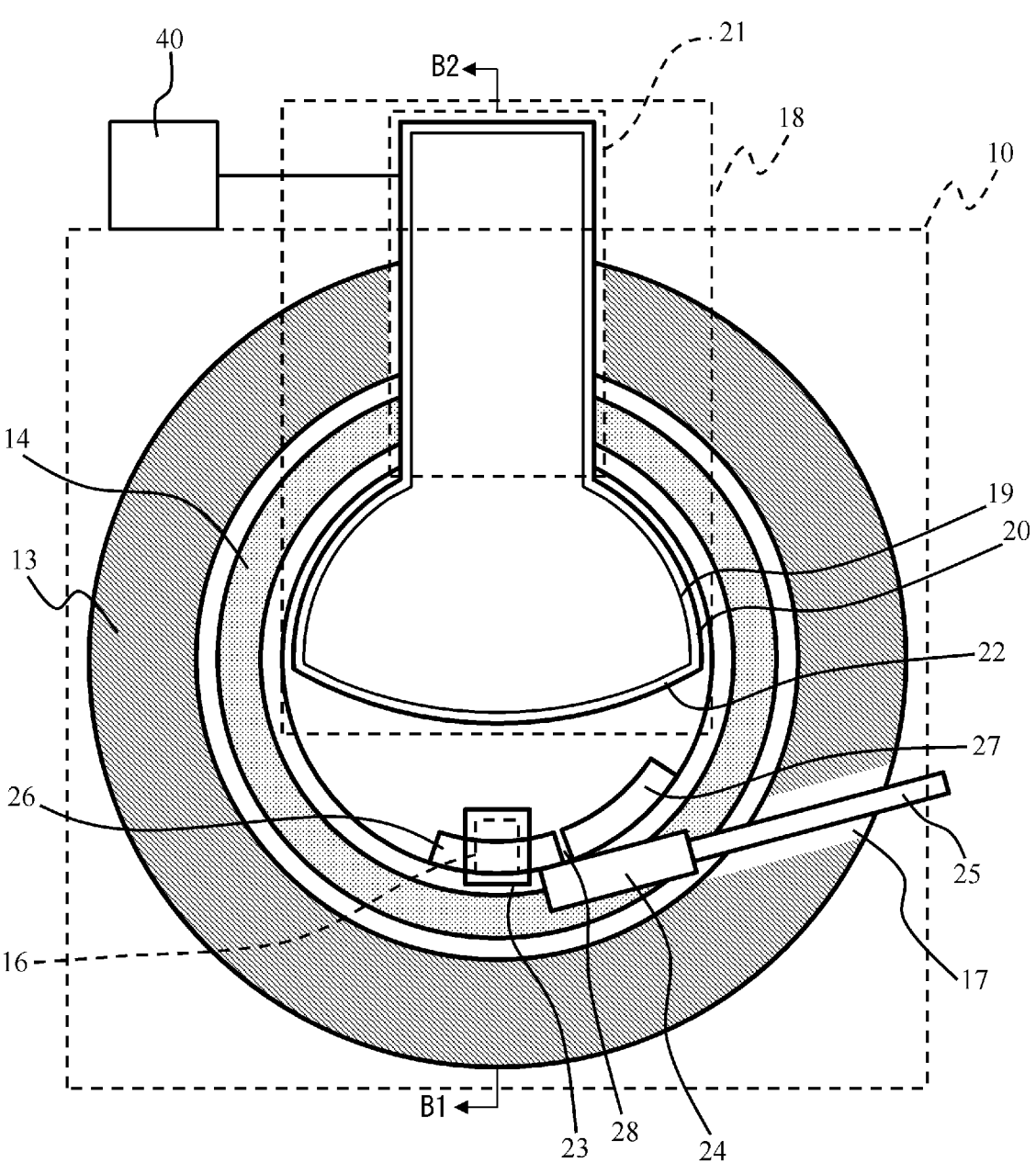
FIG. 1 is a schematic diagram illustrating a cross section taken along a plane parallel to a beam orbit of a circular accelerator.

Hereinafter, embodiments of the present invention will be described with reference to the accompanying drawings. In the present embodiment, as will be described later, by positioning the border between a peeler magnetic field 26 and a regenerator magnetic field 27 on the downstream side of an orbit aggregation region 16 in the beam traveling direction, when the amplitude of the horizontal betatron oscillation is increased with the orbit aggregation region 16 as a node, the gradient of the peeler-shaped magnetic field 26 and the gradient of the regenerator magnetic field 27 are simultaneously increased, the balance between the convergence force and the divergence force in the vertical direction can be maintained, and beam loss can be suppressed.

The present embodiment discloses a circular accelerator 1 that accelerates and extracts charged particle beam circulating in a magnetic field. The circular accelerator 1 includes a first magnetic field region 26 in which closed trajectories 30, 31, 32, and 33 of charged particle beams with different energies are eccentric and which has a magnetic field gradient increasing in magnetic field strength toward the outer peripheral side of the circular accelerator 1 and a second magnetic field region 27 having a magnetic field gradient decreasing in magnetic field strength toward the outer peripheral side of the circular accelerator 1. The border between the first magnetic field region 26 and the second magnetic field region 27 is on the downstream side in the beam traveling direction with respect to the region 16 in which the intervals between the closed trajectories with the respective energies become narrower.

According to the present embodiment, it is possible to implement a circular accelerator that can apply a large current regardless of beam energy and a particle beam therapy system that can shorten the time required for the irradiation of a beam.

First Embodiment

Figure 2:
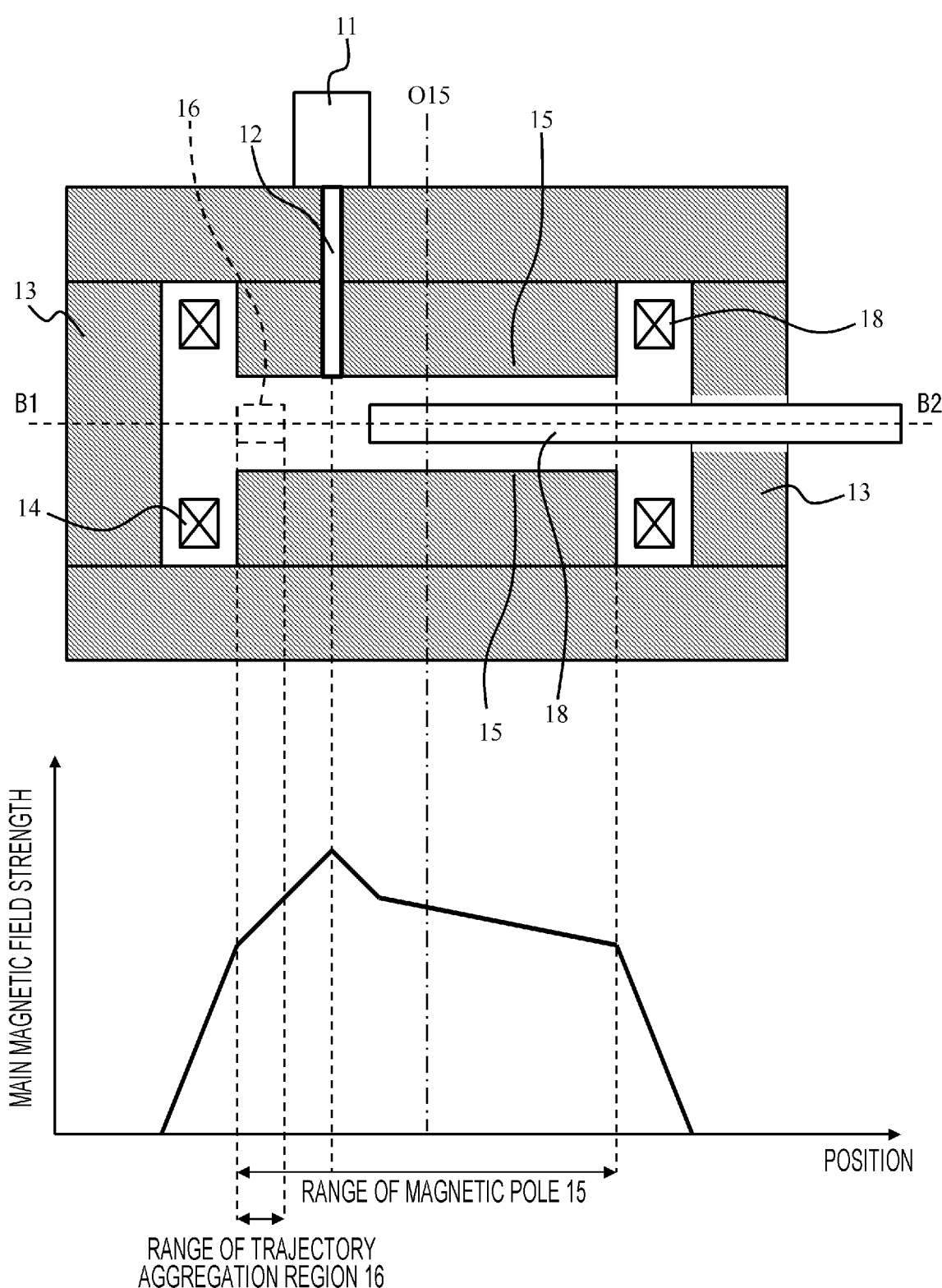
FIG. 2 is an explanatory diagram illustrating a relationship between a cross section taken along a plane perpendicular to a beam orbit of a circular accelerator and the strength of a main magnetic field.

The first embodiment will be described with reference to FIGS. 1 to 5. FIG. 1 is a schematic diagram of a cross section parallel to a beam orbit plane of a circular accelerator 1. FIG. 2 is a schematic view of a cross section taken along arrows B1-B2 in FIG. 1 and is a schematic view of a cross section perpendicular to a beam orbit plane of the circular accelerator 1.

The outer shell of the circular accelerator 1 is formed by a main electromagnet 10 that can be divided in the vertical direction in FIG. 2. A space (hereinafter, referred to as a beam circulation region) through which the beam passes is provided inside the main electromagnet 10, and the beam circulation region is held in vacuum.

An ion source 11 that generates a beam to enter the circular accelerator 1 is installed above the main electromagnet 10. The beam generated by the ion source 11 enters the beam circulation region inside the main electromagnet 10 via a low energy beam transport system 12. As the ion source 11, for example, an electron cyclotron resonance (ECR) ion source can be applied.

Note that the ion source 11 may be disposed in the beam circulation region. In this case, a penning ionization gauge (PIG) type ion source or the like can be used. When the PIG type ion source is used, the circular accelerator 1 can be downsized in the height direction.

The main electromagnet 10 includes, for example, magnetic poles 15, a yoke 13, and a coil 14. The yoke 13 forms the external appearance of the main electromagnet and forms a substantially cylindrical region in the main electromagnet. The coil 14 is an annular coil and is installed along the inner wall of the yoke 13. The magnetic poles 15 are formed on the inner peripheral side of the coil 14 so as to face each other in the vertical direction.

The main electromagnet 10 is excited by applying a current to the coil 14. When the main electromagnet 10 is excited, a magnetic field distribution (hereinafter, referred to as a main magnetic field) necessary for the circulation of a beam is formed between the opposing magnetic poles 15.

The lower side of FIG. 2 shows the strength of the main magnetic field on a line B1-B2. The main magnetic field forms a non-axisymmetric distribution with respect to a central axis O15 of the magnetic pole 15. The absolute value of the magnetic field gradient on the B1 side of the peripheral portion of the magnetic pole 15 is larger than the absolute value of the magnetic field gradient on the B2 side. A region where the absolute value of the magnetic field gradient is larger at an edge portion of the magnetic pole 15 than the surroundings is referred to as an orbit aggregation region 16.

The yoke 13 is provided with a plurality of through holes 17. The through hole 17 is used, for example, for the extraction of a beam from the circular accelerator 1, the extraction of the coil 14 to the outside (not illustrated), and the installation of a radiofrequency acceleration cavity 18.

The radiofrequency acceleration cavity 18 includes, for example, a dee electrode 19, a dummy dee electrode 20, and a resonator 21. The radiofrequency acceleration cavity 18 is connected to a radiofrequency power source 40. When radiofrequency power is supplied from the radiofrequency power source 40 to the radiofrequency acceleration cavity 18, a radiofrequency voltage necessary for beam acceleration is induced in an acceleration gap 22 between the dee electrode 19 and the dummy dee electrode 20.

The circular accelerator 1 includes a radiofrequency kicker 23, a septum coil 24, and an extraction channel 25 as devices for extracting a beam. Magnetic field distributions called a peeler magnetic field 26 and a regenerator magnetic field 27 are formed on the outer periphery of the magnetic pole 15.

A procedure for accelerating and extracting a beam using the circular accelerator 1 will be described. The beam generated by the ion source 11 enters the main electromagnet 10 via the low energy beam transport system 12. The beam incident on the main electromagnet 10 is deflected by the main magnetic field generated by the main electromagnet 10 and circulates inside the main electromagnet 10. A circular closed orbit formed by the beam circulating in the main electromagnet 10 is referred to as a central orbit. The oscillation performed by a beam particle about the central orbit is referred to as betatron oscillation. A plane on which a central orbit is formed is defined as an orbit plane of the circular accelerator 1. An oscillation frequency per round of a central orbit of betatron oscillation is called tune.

Figure 3:
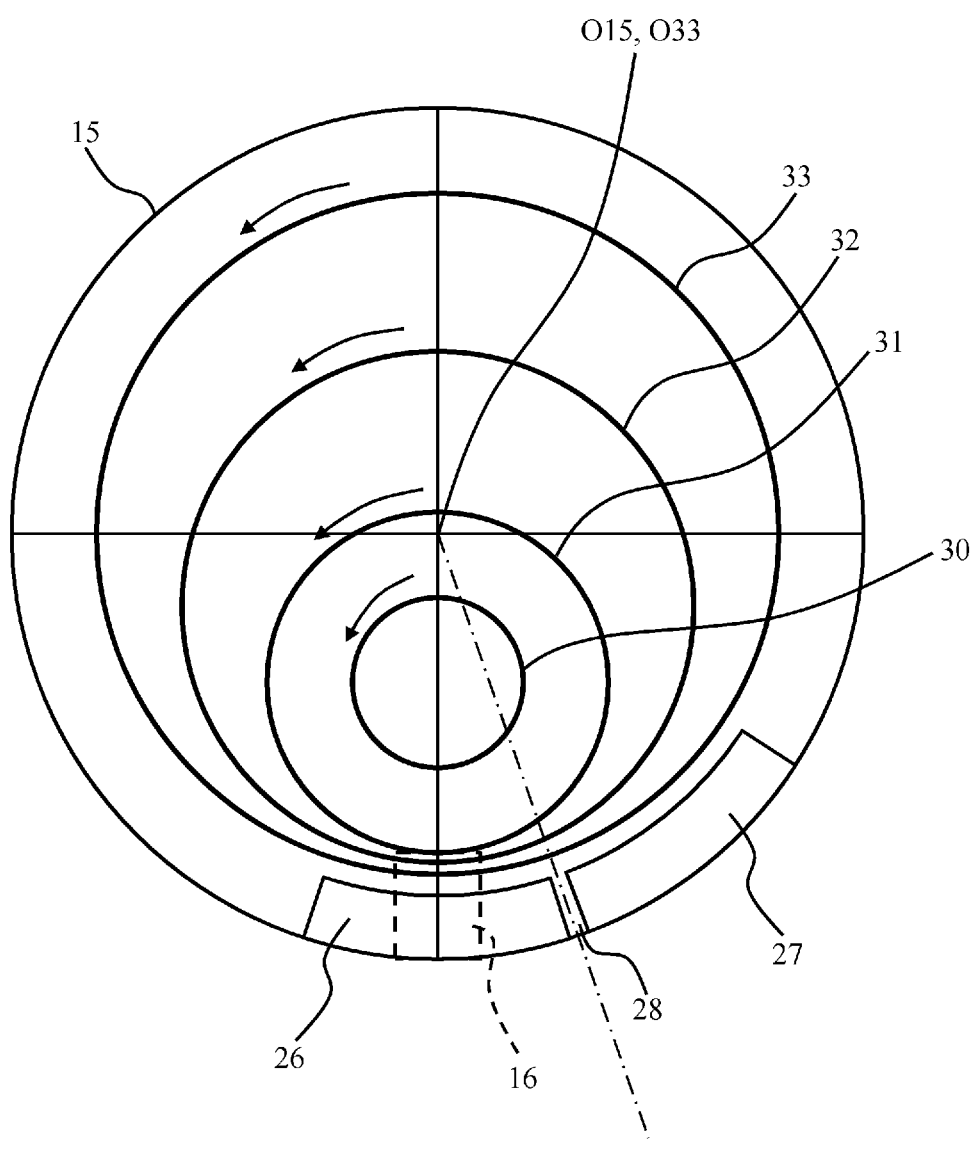
FIG. 3 is an explanatory diagram illustrating the shapes of the central trajectories of the circular accelerator.

Here, in the circular accelerator 1, since the strength of the main magnetic field is constant during an operation period, beams form different central trajectories for different energies. FIG. 3 is a schematic diagram of a central orbit for each energy in the circular accelerator 1.

A central orbit 30 from energy at beam incidence (hereinafter, referred to as incident energy) to a predetermined energy (hereinafter, the minimum extraction energy) is concentric with increasing radius as the energy increases.

A beam of energy higher than the lowest extraction energy forms an eccentric central orbit 32 such that the orbit center approaches the center of the pole 15 as the energy increases. A central orbit 31 is a central orbit at the lowest extraction energy. A central orbit 33 is a central orbit at the highest extraction energy. The energy at which the center O15 of the magnetic pole 15 and a center O33 of the central orbit coincide with each other is referred to as maximum extraction energy. In the energy region of the minimum extraction energy or more, central trajectories densely aggregate in the orbit aggregation region 16.

The acceleration gap 22 accelerates a beam to target energy by applying a radiofrequency voltage (hereinafter, referred to as an acceleration voltage) in a direction parallel to the traveling direction of the beam. The beam is accelerated in a helical orbit in a region where the energy is lower than the lowest extraction energy and accelerated in an eccentric helical orbit in a region where the energy is higher than the lowest extraction energy.

When the beam is accelerated to the target energy, the acceleration voltage applied from the acceleration gap 22 stops and the beam circulates in the main magnetic field with constant energy. The target energy at which the beam acceleration is stopped is selected in a range from the lowest extraction energy to the highest extraction energy according to the application of the circular accelerator 1.

After the acceleration of the beam is stopped, the radiofrequency kicker 23 applies a horizontal radiofrequency voltage (hereinafter, referred to as an extraction voltage) to the beam to increase the amplitude of the horizontal betatron oscillation of the beam particle. Since the radiofrequency kicker 23 is installed in the orbit aggregation region 16, a radiofrequency voltage can be applied to all the energies in the extraction range by one radiofrequency kicker 23.

Since the circulating frequency of the beam depends on energy, the frequency of the extraction voltage is controlled to a value suitable for increasing the amplitude of the horizontal betatron oscillation. More specifically, when the circulating frequency of the beam is $F_B$, the horizontal tune of the beam is $N_x$, and n is a natural number, the frequency $F_R$ of the radiofrequency voltage is set in the vicinity of equation 1 or 2.

$$F_R = nF_BN_x \qquad \text{(equation 1)}$$

$$F_R = nF_B(1 - N_x) \qquad \text{(equation 2)}$$

A beam particle with the increased amplitude of horizontal betatron oscillation comes into contract with the peeler magnetic field 26 and the regenerator magnetic field 27, which are located further on the outer circumferential side of the central orbit at the highest extraction energy.

The peeler magnetic field 26 is a magnetic field that weakens the strength of the main magnetic field as it goes away from the center of the magnetic pole 15. The regenerator magnetic field 27 is a magnetic field that increases the strength of the main magnetic field as it goes away from the center of the magnetic pole 15. In order to form the peeler magnetic field 26 and the regenerator magnetic field 27, the magnetic pole 15 is formed with a shim structure (not shown) that changes the magnetic field distribution.

The peeler magnetic field and the regenerator magnetic field may be formed using a coil for magnetic field correction disposed in the main electromagnet 10. When the peeler magnetic field 26 and the regenerator magnetic field 27 are formed using coils, the strength of the peeler magnetic field and the regenerator magnetic field can be adjusted according to the energy of the extracted beam. Both the shim structure formed in the magnetic pole 15 and the magnetic field correction coil may be used to form the peeler magnetic field 26 and the regenerator magnetic field 27. In this case, the strength of the peeler magnetic field 26 and the regenerator magnetic field 27 can be adjusted while suppressing the current required for the magnetic field correction coil.

The amplitude of the horizontal betatron oscillation of the beam particles in contact with the peeler magnetic field 26 and the regenerator magnetic field 27 rapidly increases due to the resonance of the betatron oscillation and is incident on the septum coil 24 for beam extraction. The septum coil 24 deflects the beam in a direction away from the center of the magnetic pole 15 or in a direction approaching the center of the magnetic pole 15. As a result, the beam is extracted from the through hole 17 to the outside of the accelerator 1.

The direction and amount in which the septum coil 24 deflects the beam are adjusted according to the energy of an extracted beam. A plurality of septum coils 24 may be used to extract beams. In this case, the horizontal position and the gradient (the rate of change of the horizontal position along the beam traveling direction) of the beam extracted from the circular accelerator 1 can be independently adjusted.

Instead of the septum coil 24, a magnetic field correction structure (hereinafter, referred to as a magnetic channel) made of a magnetic material such as iron may be used to extract a beam. While the magnetic channel does not require a power source for excitation, the magnetic field strength cannot be adjusted according to the energy of a beam. However, by using the magnetic channel and the septum coil 24 in combination, beams having different energies can be extracted from the same position while suppressing the excitation current of the septum coil 24.

A method for improving the efficiency of extracting a beam from the circular accelerator 1 will be described. The peeler magnetic field 26 has a function of converging a beam in the vertical direction. The regenerator magnetic field 27 has a function of diverging a beam in the vertical direction. Therefore, the beam particles in contact with the peeler magnetic field 26 and the regenerator magnetic field 27 circulate in the main magnetic field while receiving both the convergence force from the peeler magnetic field 26 and the divergence force from the regenerator magnetic field 27 in the vertical direction.

When the convergence force by the peeler magnetic field 26 is stronger than the divergence force by the regenerator magnetic field 27, the vertical tune of the beam particle increases. On the other hand, when the convergence force by the peeler magnetic field 26 is weaker than the divergence force by the regenerator magnetic field 27, the vertical tune of the beam particle decreases. The vertical tune of the circular accelerator 1 is adjusted to be in a range of 0 or more and 0.5 or less in a state before the beam particles come into contact with the peeler magnetic field 26 and the regenerator magnetic field 27.

In a case where the vertical tune increases and approaches 0.5 and a case where the vertical tune decreases and approaches 0, resonance occurs in the betatron oscillation in the vertical direction, the amplitude of the vertical betatron oscillation rapidly increases, and a beam loss occurs. For this reason, the strengths of the peeler magnetic field 26 and the regenerator magnetic field 27 need to be set so that the vertical tune of the beam particle does not change significantly.

In the circular accelerator 1, the orbit aggregation region 16 is formed in order to extract beams of different energies. Similarly to the peeler magnetic field 26, the main magnetic field in the orbit aggregation region 16 changes in a direction of weakening the main magnetic field as it goes away from the center of the magnetic pole 15.

The peeler magnetic field 26 and the regenerator magnetic field 27 form a magnetic field distribution such that the absolute value of the strength increases nonlinearly with respect to the distance from the central orbit in order to obtain a magnetic field of the strength required for extraction while suppressing the influence on the beam during acceleration. More specifically, the peeler magnetic field 26 and the regenerator magnetic field 27 are formed so as to have a hexapolar magnetic field component whose strength is proportional to the square of the distance from the central orbit. Therefore, the absolute value of the magnetic field gradient formed by the peeler magnetic field 26 and the regenerator magnetic field 27 increases as the distance from the central orbit increases. On the other hand, the gradient of the main magnetic field of the orbit aggregation region 16 is unnecessary for extracting a beam while it is necessary to apply a convergence force to the beam during acceleration. Therefore, the main magnetic field of the orbit aggregation region 16 has a constant magnetic field gradient regardless of the distance from the central orbit.

Figure 4:
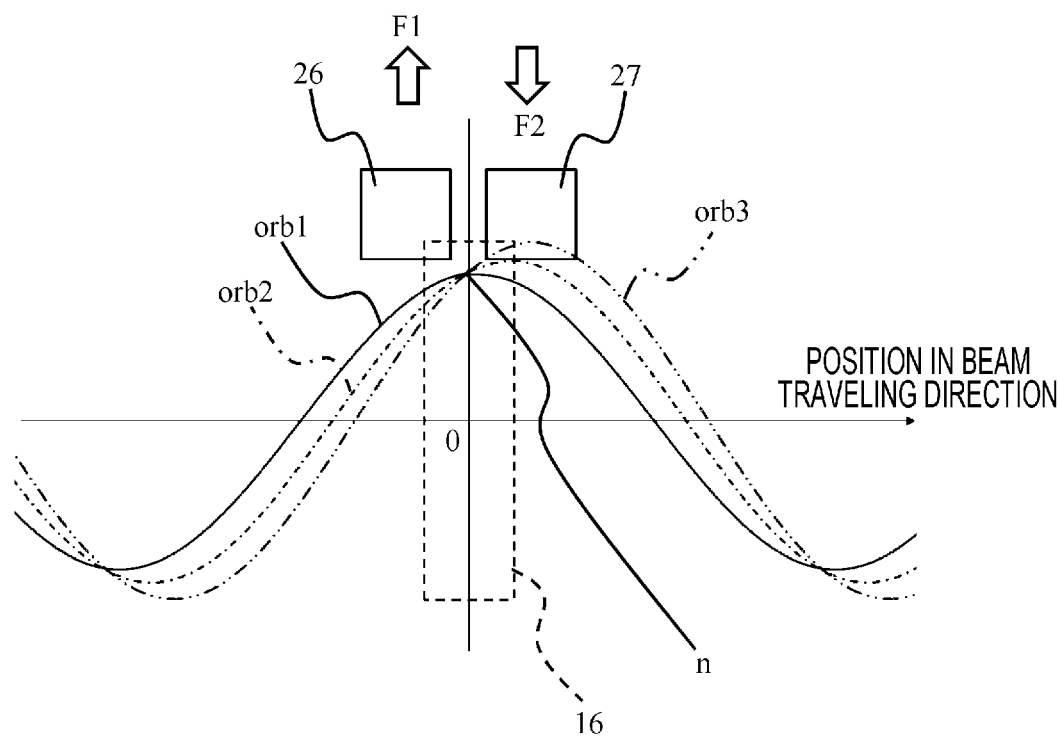
FIG. 4 is an explanatory diagram illustrating a change in the distance from the central orbit of a beam particle in contact with a peeler magnetic field and a regenerator magnetic field in a comparative example in which the peeler magnetic field and the regenerator magnetic field are arranged with an orbit aggregation region interposed therebetween.
Figure 5:
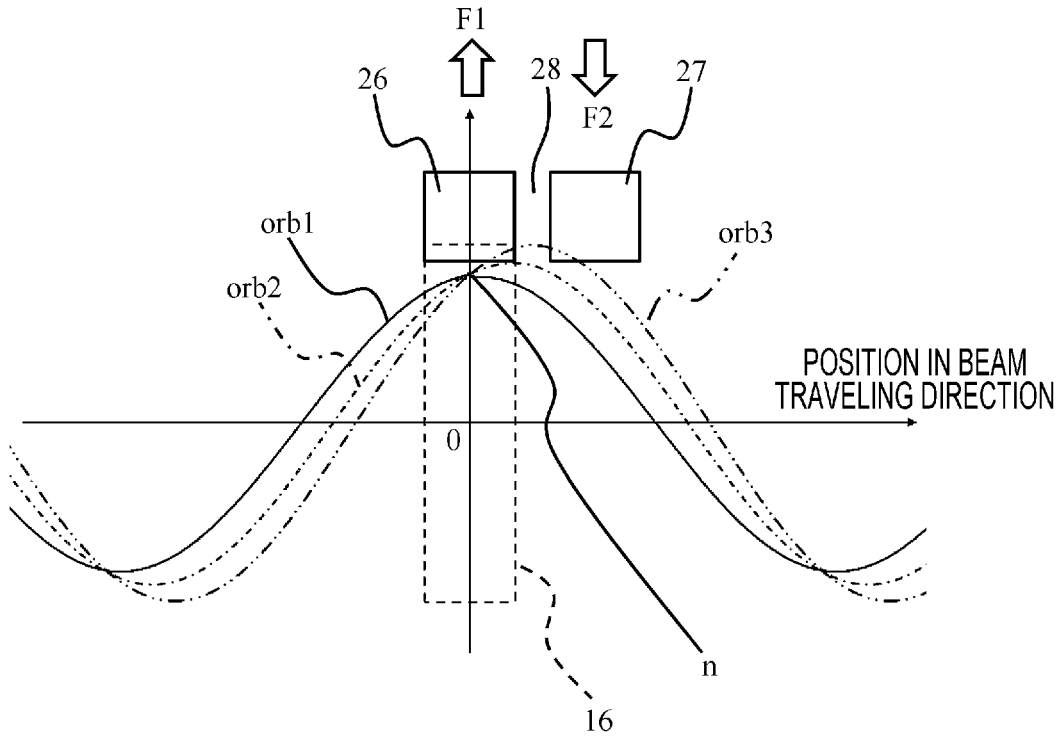
FIG. 5 is an explanatory diagram illustrating a change in the distance from the central orbit of a beam particle in contact with a peeler magnetic field and a regenerator magnetic field in the magnetic field arrangement in the first embodiment.

With reference to FIGS. 4 and 5, a change in the distance from the central orbit of the beam particle in contact with the peeler magnetic field 26 and the regenerator magnetic field 27 will be described. FIG. 4 is a schematic diagram of a configuration compared to the present embodiment. FIG. 5 is a schematic diagram of the configuration of the present embodiment.

In the comparative example illustrated in FIG. 4, the peeler magnetic field 26 and the regenerator magnetic field 27 are arranged substantially uniformly with the orbit aggregation region 16 interposed therebetween. In the present embodiment illustrated in FIG. 6, a border 28 between the peeler magnetic field 26 and the regenerator magnetic field 27 is set on the downstream side of the orbit aggregation region 16. That is, in the present embodiment, the pair of the peeler magnetic field 26 and the regenerator magnetic field 27 is shifted to the downstream side in the beam progressing direction. The horizontal axis in FIGS. 4 and 5 represents the position in the beam traveling direction. An intersection point 0 with the vertical axis corresponds to the orbit aggregation region 16.

When a peeler-shaped magnetic field (the peeler magnetic field 26 and the magnetic field of the orbit aggregation region 16) and the regenerator magnetic field 27 are applied to beam particles, the amplitude of the horizontal betatron oscillation increases so that the peeler-shaped magnetic field becomes a node n as illustrated in FIGS. 4 and 5. In the vicinity of the central orbit, since the magnetic field change of the orbit aggregation region 16 is larger than the magnetic field change of the peeler magnetic field 26, the amplitude of the horizontal betatron oscillation increases with the orbit aggregation region 16 as the node n.

In the comparative example of FIG. 4 in which the peeler magnetic field 26 and the regenerator magnetic field 27 are arranged with the orbit aggregation region 16 interposed therebetween, the magnetic field gradient of the regenerator magnetic field 27 increases with an increase in the amplitude of the horizontal betatron oscillation, whereas the magnetic field gradient of the orbit aggregation region 16 does not change from the initial state. Since the convergence and divergence forces in the vertical direction are proportional to the magnetic field gradient, in the comparative example of FIG. 4, the divergence force in the vertical direction becomes dominant due to the increase in the amplitude of the horizontal betatron oscillation, and the vertical tune approaches 0 to cause a beam loss.

On the other hand, in the present embodiment illustrated in FIG. 5, since the border 28 between the peeler magnetic field 26 and the regenerator magnetic field 27 is located on the downstream side of the orbit aggregation region 16 in the beam traveling direction, when the amplitude of the horizontal betatron oscillation increases with the orbit aggregation region 16 as the node n, the strength of the peeler-shaped magnetic field received by the beam particle simultaneously increases nonlinearly.

As a result, in the present embodiment, when the amplitude of the horizontal betatron oscillation increases, the gradient of the peeler-shaped magnetic field and the gradient of the regenerator magnetic field 27 simultaneously increase, so that the balance between the convergence force and the divergence force in the vertical direction is maintained, and the occurrence of a beam loss is suppressed.

Referring to FIGS. 1 and 5, the center of the peeler magnetic field 26 is matched with the center of the orbit aggregation region 16, but the present invention is not limited thereto. As long as the condition that the border 28 between the peeler magnetic field 26 and the regenerator magnetic field 27 is located on the downstream side of the center of the orbit aggregation region 16 is satisfied, the center of the peeler magnetic field 26 may be set to another location. When the center of the peeler magnetic field 26 is set upstream of the center of the orbit aggregation region 16, the regenerator magnetic field 27 approaches the orbit aggregation region 16, and hence, it is easy to bring particularly low-energy beam particles into contact with the regenerator magnetic field 27.

Second Embodiment

Figure 6:
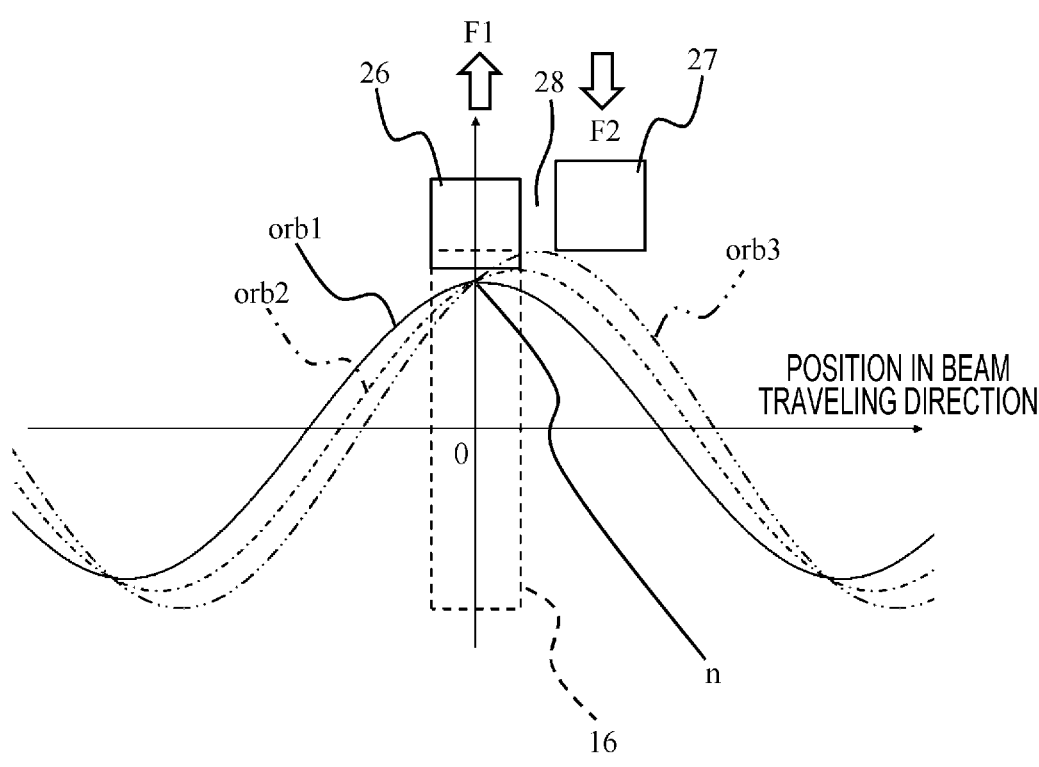
FIG. 6 is an explanatory diagram illustrating a change in the distance from the central orbit of a beam particle in contact with a peeler magnetic field and a regenerator magnetic field in a case where the regenerator magnetic field is installed radially outside the peeler magnetic field according to the second embodiment.

The second embodiment will be described with reference to FIG. 6. In the following embodiments including the present embodiment, differences from the first embodiment will be mainly described. FIG. 6 is a schematic diagram illustrating a change in the distance from the central orbit of the beam particle in contact with a peeler magnetic field 26 and a regenerator magnetic field 27.

In the present embodiment, the regenerator magnetic field 27 is disposed closer to the outer circumferential side of the magnetic pole than the peeler magnetic field 26. In this case, since it is possible to suppress the beam particle with the increased amplitude of the horizontal betatron oscillation from coming into contact with the regenerator magnetic field 27 before the peeler magnetic field 26, it is possible to suppress the occurrence of resonance in the vertical direction more effectively than the first embodiment.

Third Embodiment

Figure 7:
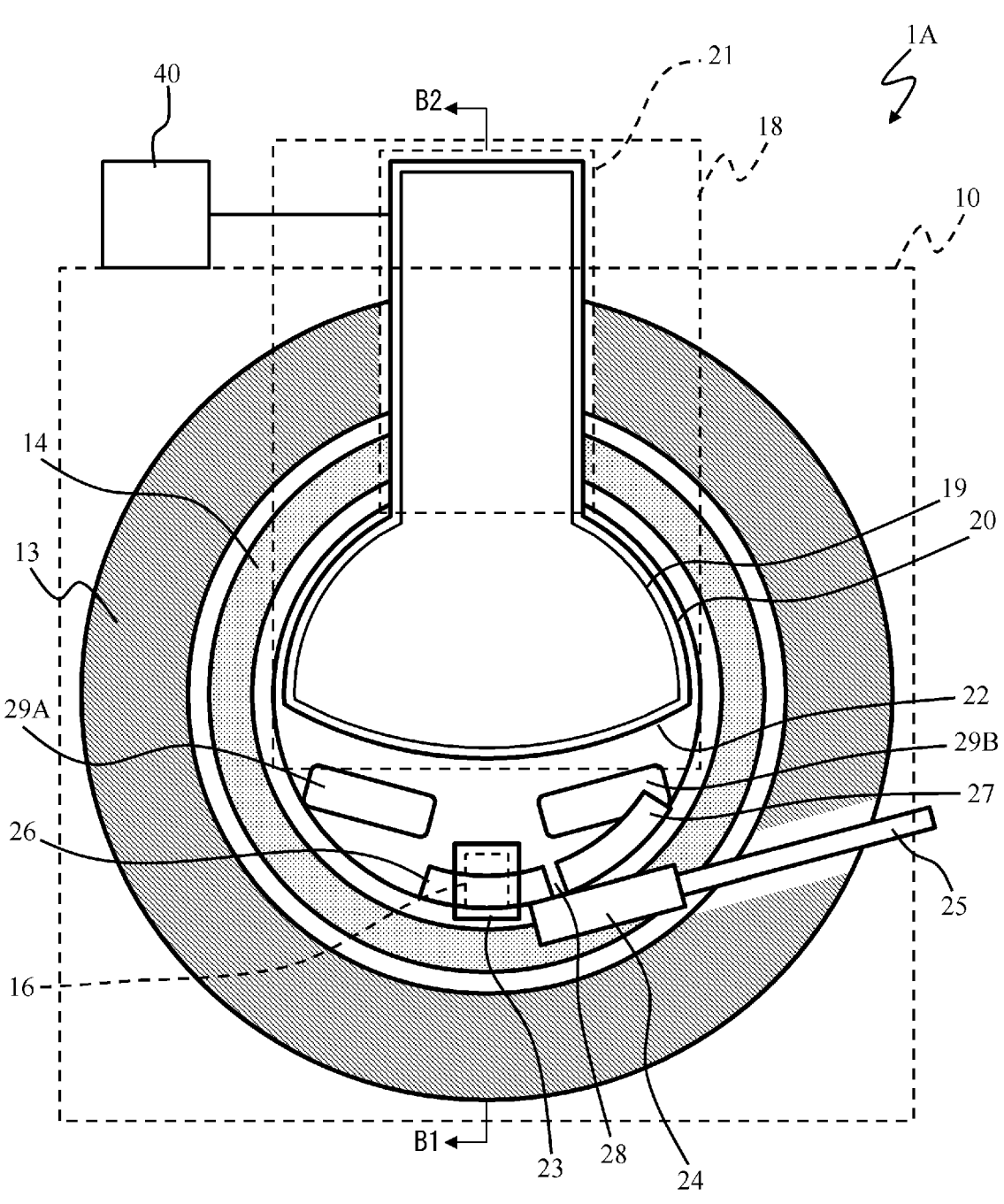
FIG. 7 is a schematic diagram illustrating a cross section taken along a plane parallel to a beam orbit of a circular accelerator according to the third embodiment.
Figure 8:
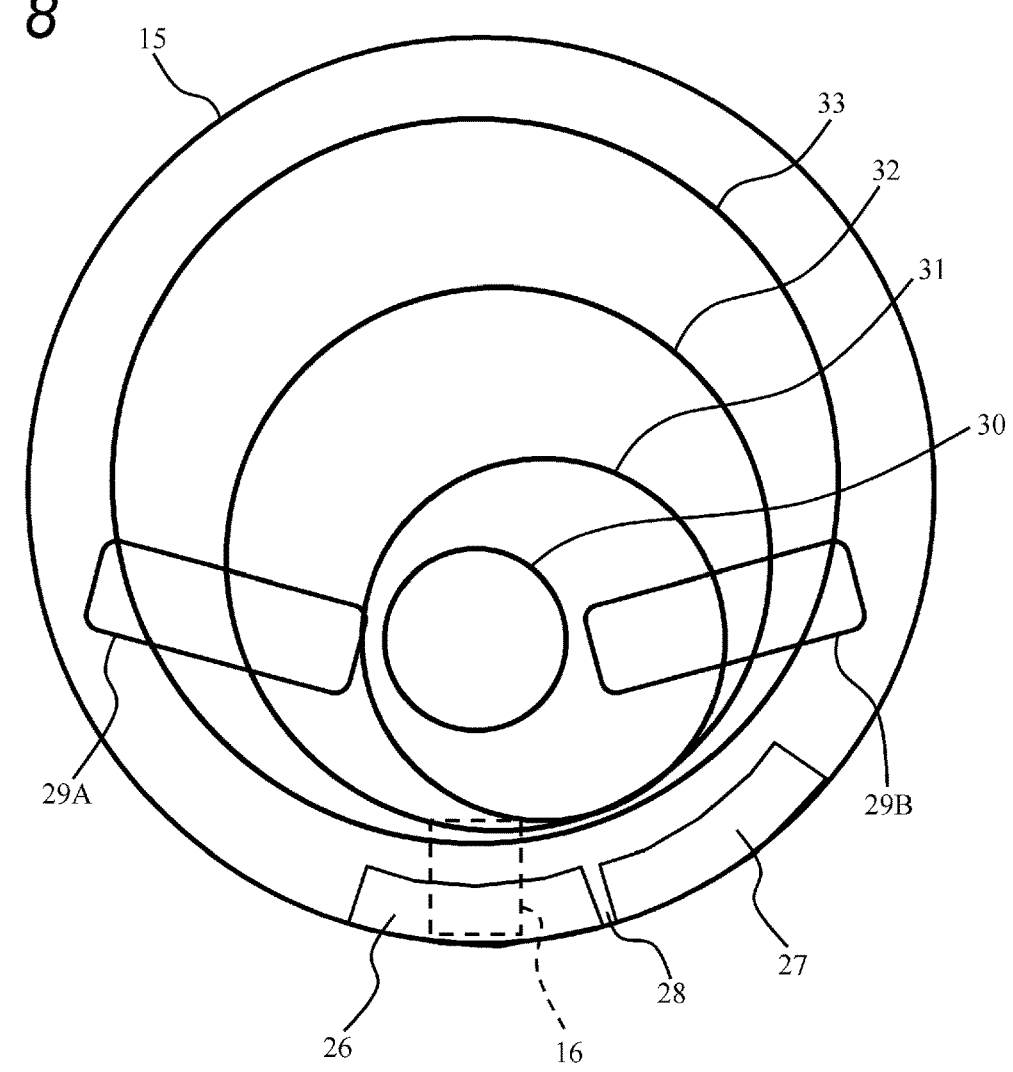
FIG. 8 is an explanatory diagram illustrating the shapes of central trajectories of a circular accelerator.

The third embodiment will be described with reference to FIGS. 7 and 8. A circular accelerator 1A according to the present embodiment has orbit correction magnetic fields 29A and 29B. The circular accelerator 1A according to the present embodiment has the same configuration as the circular accelerator 1 described in the first embodiment but is different from the first embodiment in that the orbit correction magnetic fields 29A and 29B are formed on magnetic poles 15. FIG. 7 is a schematic diagram illustrating a cross section taken along a plane parallel to a beam orbit of the circular accelerator 1A.

The orbit correction magnetic field 29A is a magnetic field in a direction of weakening the main magnetic field generated by the magnetic pole 15. The orbit correction magnetic field 29B is a magnetic field in a direction of strengthening the main magnetic field generated by the magnetic pole 15. The orbit correction magnetic fields 29A and 29B are formed at symmetrical positions with an orbit aggregation region 16 interposed therebetween. The strengths of the orbit correction magnetic fields 29A and 29B have different values according to the energies of circulating beam intersecting the orbit correction magnetic fields 29A and 29B.

The orbit correction magnetic fields 29A and 29B can be formed by providing a shim structure (not illustrated) for magnetic field generation in the magnetic pole 15. The orbit correction magnetic fields 29A and 29B are formed by adopting a shim structure in which the shape of the magnetic pole 15 is partially changed so as to increase or decrease the magnetic pole interval in the vertical direction. By changing the height and width of the shim structure for each location, the strength of the orbit correction magnetic fields 29A and 29B can be changed according to energy.

The orbit correction magnetic fields 29A and 29B can also be formed by a correction magnetic field coil (not illustrated) inserted between the magnetic poles 15. In this case, the strengths of the orbit correction magnetic fields 29A and 29B are controlled by the current flowing through the correction magnetic field coil. In order to set the strengths of the orbit correction magnetic fields 29A and 29B to values corresponding to the energy of the beam extracted from the circular accelerator 1A, the current flowing through the correction magnetic field coil is adjusted to a value corresponding to the beam energy.

When the orbit correction magnetic fields 29A and 29B are formed by the correction magnetic field coil, the strengths of the orbit correction magnetic fields 29A and 29B can be adjusted after the accelerator 1A is manufactured. The orbit correction magnetic fields 29A and 29B may be formed by using a shim structure and a correction magnetic field coil in combination. In this case, since the magnetic field distribution before the current flows to the correction magnetic field coil has a value close to the state in which the necessary orbit correction magnetic fields 29A and 29B are already added, it is possible to finely adjust the strengths of the orbit correction magnetic fields 29A and 29B after the manufacture of the accelerator 1A while suppressing the strength of the current flowing to the correction magnetic field coil.

A method for improving the speed of extracting a beam from the circular accelerator 1A by the orbit correction magnetic fields 29A and 29B will be described with reference to FIG. 8. FIG. 8 is a schematic diagram of a central orbit for each energy in the circular accelerator 1A.

In the circular accelerator 1A according to the present embodiment, similarly to the first embodiment, the central trajectories in the energy region lower than the lowest extraction energy are concentric, and the central trajectories in the energy region higher than the lowest extraction energy are eccentric. Further, in the circular accelerator 1A, since the orbit correction magnetic fields 29A and 29B are applied to a circulating beam, the central orbit moves in the direction of a regenerator magnetic field 27 as the beam energy decreases in the energy region from the lowest extraction energy to the highest extraction energy. Since the movement amount of the central orbit decreases as the energy increases and becomes 0 at the maximum energy, the shape of a central orbit 33 at the maximum energy is the same as that in the first embodiment.

In the circular accelerator 1A according to the present embodiment, in order to prevent the betatron oscillation in the vertical direction from becoming unstable when a beam is extracted, a border 28 between a peeler magnetic field 26 and the regenerator magnetic field 27 is arranged on the downstream side of an orbit aggregation region 16.

A low energy beam has a smaller radius of the central orbit than a high energy beam. Thus, the lower the energy, the greater r the amplitude of the horizontal betatron oscillation required to come into contact with the regenerator magnetic field 16. As a result, in the circular accelerator 1 according to the first embodiment, it is necessary to greatly increase the amplitude of the horizontal betatron oscillation using a radiofrequency kicker 23 when extracting a low energy beam. Therefore, in the circular accelerator 1 according to the first embodiment, it takes time until beam extraction starts.

On the other hand, in the circular accelerator 1A according to the present embodiment, the central orbit of a beam is corrected so as to approach the regenerator magnetic field 27 as the energy decreases. Therefore, in the circular accelerator 1A, the amplitude of the horizontal betatron oscillation necessary for s beam to come into contact with the regenerator magnetic field 27 in the low energy region is smaller than that in the first embodiment. As a result, in the circular accelerator 1A according to the present embodiment, it is possible to shorten the time required to start beam extraction in the low energy region and to end beam irradiation in a short time.

In the circular accelerator 1A according to the present embodiment, the central orbit is not corrected by the orbit correction magnetic fields 29A and 29B in the energy region lower than the minimum extraction energy. Therefore, the orbit correction magnetic fields 29A and 29B are not formed in an energy region lower than the lowest energy, that is, a region where the central trajectories with the respective energies are concentric. However, a spatially abrupt change in the strength of the magnetic field may impair the stability of the circulating beam. Therefore, in the energy region lower than the minimum extraction energy, the strengths of the orbit correction magnetic fields 29A and 29B are gradually attenuated as the energy decreases.

In the circular accelerator 1A according to the present embodiment, the orbit correction magnetic fields 29A and 29B are formed symmetrically with respect to the orbit aggregation region 16, but this is an example. The orbit correction magnetic fields 29A and 29B may have any shape as long as the distribution causes central trajectories to approach the regenerator magnetic field as a whole. The orbit correction magnetic fields 29A and 29B may not be formed symmetrically with respect to the orbit aggregation region 16.

On the other hand, forming the orbit correction magnetic fields 29A and 29B symmetrically with respect to the orbit aggregation region 16 has an advantage that the movement amount of a central orbit can be easily calculated. The orbit correction magnetic field may be formed at one place or three or more places. When orbit correction magnetic fields are formed at a plurality of places, the strength of the orbit correction magnetic field per place is reduced. For this reason, the shim structure and the magnetic field correction coil can be easily manufactured, but the design of the magnetic field distribution becomes complicated.

The circular accelerator 1A according to the present embodiment improves the beam extraction efficiency similarly to the circular accelerator 1 according to the first embodiment. Furthermore, in the circular accelerator 1A according to the present embodiment, the time until the beam extraction can be shortened in the extraction of a low energy beam, so that the average beam current can be improved. Thus, when the circular accelerator 1A according to the present embodiment is used in the particle beam therapy system, treatment can be completed in a shorter time than when the circular accelerator 1 described in the first embodiment is used in the particle beam therapy system.

Fourth Embodiment

Figure 9:
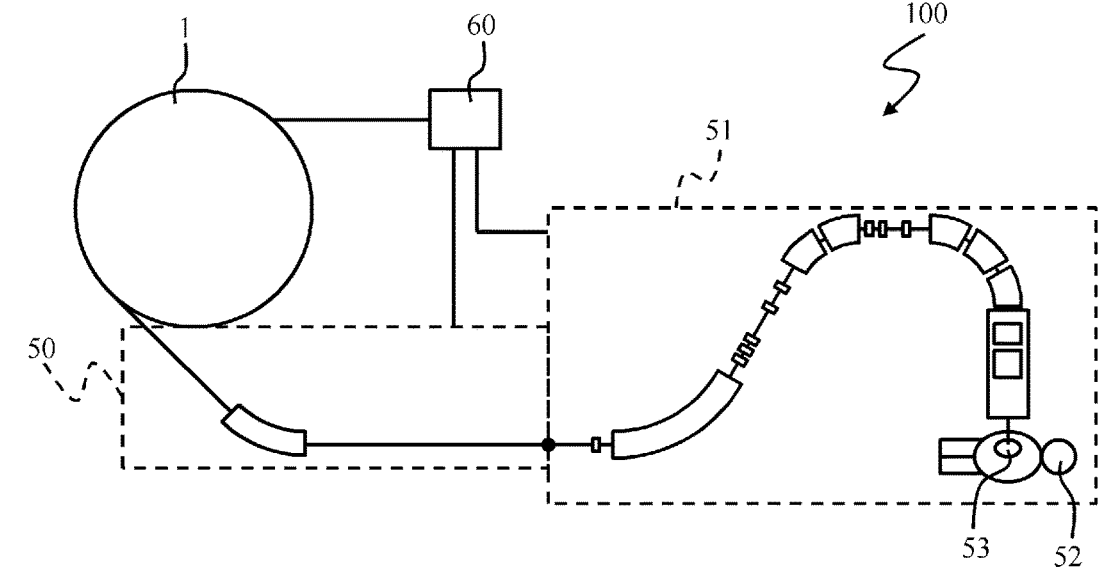
FIG. 9 is a schematic diagram of a particle beam therapy system using a circular accelerator according to the fourth embodiment.

A particle beam therapy system 100 using a circular accelerator 1 will be described with reference to FIG. 9. The particle beam therapy system 100 illustrated in FIG. 9 includes, for example, the circular accelerator 1, a beam transport system 50, and a rotating gantry 51, and these main components 1, 50, and 51 are connected to a control system 60.

The control system 60 operates the circular accelerator 1, controls the beam transport system 50 and the rotating gantry 51 based on a treatment plan created in advance by a treatment planning device (not illustrated), and irradiates an affected area 53 of a patient 52 with a beam.

The particle beam therapy system 100 can change the energy of the beam extracted from the circular accelerator 1 in a range (for example, a range of 70 MeV to 230 MeV) used in a particle beam therapy. Therefore, the particle beam therapy system 100 need not install a degrader for adjusting the energy applied to the patient 52 in the middle of the beam transport system 50 as s in, for example, a particle beam therapy system using a cyclotron in an accelerator.

The particle beam therapy system 100 according to the present embodiment can prevent the occurrence of a beam loss in the degrader and thus can obtain a high beam current regardless of the energy of the beam with which the patient 52 is irradiated. Furthermore, since the particle beam therapy system 100 according to the present embodiment can suppress a beam loss at the time of extracting a beam from the circular accelerator 1, the current of the beam with which the patient 52 is irradiated can be improved, and the treatment can be completed in a shorter time.

Note that the present invention is not limited to the above-described embodiments. Those skilled in the art can make various additions and modifications within the scope of the present invention. In the above-described embodiment, the present invention is not limited to the configuration examples illustrated in the accompanying drawings. The configuration and the processing method according to each embodiment can be appropriately changed within the scope of achieving the object of the present invention.

In addition, each constituent element of the present invention can be arbitrarily selected, and an invention having a selected configuration is also included in the present invention. Further, the configurations described in the claims can be combined in manners other than the combinations specified in the claims.

REFERENCE SIGNS LIST 1 circular accelerator
10 main electromagnet

12

11 ion source
12 low energy beam transport system
13 yoke
14 coil
15 magnetic pole
16 orbit aggregation region
17 through hole
18 radiofrequency acceleration cavity
19 dee electrode
20 dummy dee electrode
21 resonator
22 acceleration gap
23 radiofrequency kicker
24 septum coil
25 channel
26 peeler magnetic field
27 regenerator magnetic field
28 border
29A, 29B orbit correction magnetic field
30 to 33 central orbit
40 radiofrequency power source
50 beam transport system
51 rotating gantry
60 control system
100 particle beam therapy system

The invention claimed is:

1. A circular accelerator that accelerates and extracts charged particle beams circulating in a magnetic field, the circular accelerator comprising:
a first magnetic field region in which closed trajectories of the beams with different energies are eccentric and which has a magnetic field gradient decreasing in the magnetic field toward an outer peripheral side; and
a second magnetic field region having a magnetic field gradient increasing in the magnetic field toward an outer peripheral side,
wherein a border between the first magnetic field region and the second magnetic field region is located on a downstream side in a traveling direction of the beam with respect to a predetermined region in which an interval between the closed trajectories of the beams with the different energies is narrowest.

2. The circular accelerator according to claim 1, wherein the border between the first magnetic field region and the second magnetic field region is located on a downstream side in the traveling direction of the beam with respect to a predetermined region in which an interval between closed trajectories of the beams with different energies is narrowest, and a center of the first magnetic field region in the beam traveling direction is located on an upstream side in the beam traveling direction with respect to the predetermined region.

3. The circular accelerator according to claim 1, wherein the border between the first magnetic field region and the second magnetic field region exists in a range from a point located downstream of the predetermined region in the traveling direction of the beam to a point less than 90°.

4. The circular accelerator according to claim 1, wherein a distance from a central orbit of the beam to the second magnetic field region is larger than a distance from the central orbit of the beam to the first magnetic field region.

5. A particle beam therapy system using the circular accelerator according to claim 1.

* * * * *